United States Patent [19]

Grossman

[11] Patent Number: 5,387,558
[45] Date of Patent: Feb. 7, 1995

[54] COLORED GLASS-CERAMIC ARTICLES

[75] Inventor: David G. Grossman, Corning, N.Y.

[73] Assignee: Corning Incorporated, Corning, N.Y.

[21] Appl. No.: 236,088

[22] Filed: May 2, 1994

[51] Int. Cl.$^6$ ............................................. C03C 10/16
[52] U.S. Cl. ........................................ 501/3; 501/57;
    501/64; 501/69; 501/72; 106/35
[58] Field of Search ............... 501/3, 57, 64, 69, 72;
    252/301.4 H; 106/35

[56] References Cited

U.S. PATENT DOCUMENTS

| | | |
|---|---|---|
| 1,292,148 | 1/1919 | Taylor . |
| 3,839,055 | 10/1974 | Grossman . |
| 4,170,823 | 10/1979 | Smythe . |
| 4,431,420 | 2/1984 | Adair . |
| 4,575,805 | 3/1986 | Moermann et al. . |
| 4,652,312 | 3/1987 | Grossman et al. . |
| 4,663,720 | 5/1987 | Duret et al. . |
| 4,664,629 | 5/1987 | Chodkowski . |

FOREIGN PATENT DOCUMENTS 0083828  1/1982  European Pat. Off. .

OTHER PUBLICATIONS

W. A. Weyl in "Coloured Glasses", Dawson's of Pall Mall, London, England, 1959, pp. 213 and 233.

*Primary Examiner*—Karl Group
*Attorney, Agent, or Firm*—C. S. Janes, Jr.

[57] ABSTRACT

This invention is directed to the formation of glass-ceramic articles which exhibit a yellow coloration in visible light and fluoresce with a yellow coloration while being exposed to ultraviolet radiation. The yellow coloration is produced through the incorporation of a color package comprising 0.05–0.5% $V_2O_5$, 0.25–5% $CeO_2$, and 0.1–1% $Tb_2O_3$. When the glass-ceramic articles contain tetrasilicic fluormica as the predominant crystal phase, they are eminently suitable for use as dental prosthetic materials.

12 Claims, No Drawings

COLORED GLASS-CERAMIC ARTICLES

BACKGROUND OF THE INVENTION

The attainment of aesthetics in synthetic tooth filling-/covering materials demands close control over many factors. The ideal prosthetic material blends well with the restored tooth as well as with adjacent teeth under widely-varying conditions of illumination, including natural and artificial light, and even under ultraviolet or "black" light. Obviously, the color of the material and the ability of the material to transmit a certain fraction of the light which impinges thereon are important. Excellent aesthetics also requires that the material exhibit the capability to disperse and scatter the light through internal reflections. That capability produces a certain depth to the translucency and color which can mimic such natural materials as tooth enamel and ivory.

Glass-ceramics have been used commercially as synthetic tooth filling/covering materials and in dental prostheses [U.S. Pat. No. 4,431,420 (Adair) and U.S. Pat. No. 4,652,312 (Grossman et al.)], because of the many fine scattering centers produced by internal nucleation and controlled growth of crystals in those highly crystalline materials. Fabrication of those glass-ceramic materials into the precise shapes demanded for tooth repair and replacement has utilized several techniques, the two most commonly being practiced involving casting via the classic lost wax process and the rather recent CAD/CAM technique. [U.S. Pat. No. 4,575,805 (Moermann et al.) and U.S. Pat. No. 4,663,720 (Duret et al.)].

U.S. Pat. No. 3,839,055 (Grossman) describes a family of glass-ceramic materials identified as tetrasilicic fluormica glass-ceramics which are characterized by good strength and translucency, thereby rendering them especially well suited for the fabrication of dental constructs. European Patent No. 0083828 (Grossman) delineates a preferred range of tetrasilicic fluormica base compositions for dental applications. Those preferred base compositions consist essentially, in weight percent as calculated from the batch, of 45–70% $SiO_2$, 8–20% MgO, 8–15% $MgF_2$, 5–20% $K_2O$, 0.05–2% $Al_2O_3$, 0.5–7% $ZrO_2$, 1–9% total $ZrO_2+Al_2O_3$, 0–7% $TiO_2$, and 0–10% conventional glass colorants. The patent mentions the optional inclusion of Group II metal oxides and oxides of the metallic transition elements. U.S. Pat. No. 4,652,312, supra, describes a further improved range of tetrasilicic fluormica base compositions for dental applications. Those compositions consist essentially, in weight percent on the oxide basis, except for fluorine which is expressed on an elemental basis, of 45–70% $SiO_2$, 13–30% MgO, 5–20% $K_2O$, 4–9% F, 0–2% $Al_2O_3$, 0–7% $ZrO_2$, 1–4% BaO, and 0–5% SrO. The most preferred compositions consist essentially, in weight percent, of 55–65% $SiO_2$, 14–19% MgO, 8–18% $K_2O$, 0.05–2% $Al_2O_3$, 0.5–7% $ZrO_2$, 4–9% F, and 1–4% BaO.

In conventional dental ceramics, such as dental porcelain, where it is desired to produce a given color in the fired material, a ceramic pigment or combination of several pigments is incorporated into the composition. The crystals of the pigments remain sufficiently intact during the firing process to impart the desired color in the finished product. Ceramic pigments consist mostly of refractory crystals containing color centers frequently produced by the ions of such transition metals as Co, Cr, Fe, Mn, Ni, and V. The actual color provided by those pigments, however, is governed to a large extent by the crystalline structure of the host compound into which the transition metal ions are incorporated.

To color a glass or a glass-ceramic article, coloring ions such as those in the transition metal series are customarily added to the precursor batch as oxides or carbonates. Those compounds are dissolved in the glass during melting and the color center produced depends upon the individual ion(s) and the ligand field surrounding the ion(s), the latter being determined by the glass or amorphous structure. This method of coloring is more analogous to solution chemistry and is distinct from the prior method conventionally utilized in ceramic technology.

In the field of glass-ceramics it is quite common for the color produced in the precursor or parent glass to be different from the color developed in the crystallized glass-ceramic as a result of heat treating the parent glass. This change is brought about through the alteration in the amorphous structure which occurs to the composition of the residual glass as the components comprising the crystals are removed therefrom. There may also be some incorporation of the coloring ions into the crystals of the glass-ceramic which would likewise alter the ligand field surrounding the coloring ions.

In order to produce acceptable colors for use in dental glass-ceramics, colorants are needed which produce yellow to yellow-red or tan in the crystallized product. Unfortunately, no single transition metal or rare earth metal ion has been identified which yields a clear yellow effect with the exception of uranium. Governmental regulations regarding radioactivity restrict the use of uranium. However, a method for combining certain pairs of ions to gain an interactive effect leading to yellow colors has been described by W. A. Weyl in "Coloured Glasses", Dawson's of Pall Mall, London, England, 1959.

For example, Weyl reports the use of $CeO_2$ which, by itself produces no color in glass, but which, in combination with $TiO_2$ imparts strong yellow colors. That yellow color can be modified by incorporating the rare earth metal oxide $Er_2O_3$ therein, and other color modifiers may be utilized to vary the shade produced. Whereas the combination of $CeO_2$ and $TiO_2$ with, perhaps, other modifying oxides works well in visible light, fluorescence under long wave ultraviolet illumination does not take place because the presence of $TiO_2$ strongly absorbs ultraviolet radiation.

Therefore, the primary objective of the present invention was to devise glass-ceramic compositions which would exhibit a range of yellow colorations in the visible portion of the radiation spectrum, coupled with the ability to fluoresce under ultraviolet illumination. Such glass-ceramic materials would be especially useful as dental prosthetic materials in that their colors can be modified to blend well with a restored tooth as well as with adjacent teeth under various conditions of illumination, including visible and ultraviolet light.

SUMMARY OF THE INVENTION

That objective can be achieved through the use of a critical combination of $CeO_2$, $V_2O_5$, and $Tb_2O_3$ to provide the coloration.

U.S. Pat. No. 1,292,148 (Taylor) discloses the use of a combination of $CeO_2$ and $V_2O_5$ in soda lime silica glass to produce a very pale yellow color therein. The glasses were designed for use as filters for ultraviolet radiation.

One objective of that invention was to produce glasses as colorless as possible in the visible portion of the radiation spectrum.

$CeO_2$ acts as a strong fluorescing agent in a glass or glass-ceramic and imparts a white to blue-white fluorescence under long wave (366 nm) ultraviolet light. Increasing additions of $V_2O_5$, to glass-ceramic formulations containing a constant level of $CeO_2$ act to diminish the intensity of fluorescence therein. Small quantities of $V_2O_5$, however, can be employed (generally less than 0.5% by weight, preferably no more than 0.3%, but at least 0.05%) which can easily provide coloration in visible light and which will allow a sufficient level of fluorescence. The preferred coloration is induced with 0,075–0.2% $V_2O_5$. At first glance it would seem plausible to simply increase the $CeO_2$ content in order to enhance the intensity of fluorescence. Surprisingly, raising the level of $CeO_2$ at a constant concentration of $V_2O_5$ results in a reduction in the intensity of fluorescence.

It has been conjectured that the most likely explanation for this phenomenon resides in a shift taking place in the equilibrium existing between the various valence states of cerium and vanadium, viz.:

$$V^{4+} + Ce^{4+} = V^{5+} + Ce^{3+}$$

The pentavalent vanadium ion is thought to be responsible for producing a yellow-red color in the glass-ceramic. The trivalent cerium ion can likewise contribute a yellow tint in the visible portion of the radiation spectrum, but its primary action is to absorb in the ultraviolet region of the spectrum, thereby interfering with the desired fluorescence. Consequently, the obtention of a useful visible color with adequate fluorescence is only possible by carefully balancing the $CeO_2$ and $V_2O_5$ contents. The concentration of $CeO_2$ must not exceed 5% by weight with a preferred maximum of 3% and a minimum of 0.25%. The most desirable amounts will range about 0.5–2%, depending upon the levels of $V_2O_5$ and $Tb_2O_3$ and the base composition of the glass-ceramic. If insufficient $CeO_2$ is present, the equilibrium in the above equation shifts to the left such that excessive tetravalent vanadium is produced. The $V^{4+}$ ion produces a blue color in both the precursor glass and the crystallized glass-ceramic.

When the correct balance has been achieved between the levels of cerium and vanadium, two other tasks remain. First, to obtain the desired color in the visible portion of the spectrum, and, second, to obtain the desired color of the fluorescence.

The tint in visible light can be modified through the inclusion of relatively inert colorants; i.e., colorants which do not markedly shift the cerium-vanadium equilibrium. Examples of such colorants are $Er_2O_3$ for red, $MnO_2$ or $Cr_2O_3$ for gray, and NiO for dark gray. Some of those colorants, however, such as $MnO_2$, can have a tendency to diminish the intensity of fluorescence and, hence, can only be used in small quantities.

With respect to the color of the fluorescence, it must initially be observed that both $CeO_2$ and $V_2O_5$ fluoresce when exposed to long wave (366 nm) ultraviolet radiation. $CeO_2$ fluoresces a blue-white color whereas $V_2O_5$ fluoresces a yellow-orange color. The resulting mixed effect depends upon the ratio $CeO_2:V_2O_5$, but ranges from a pale neutral gray to an orange color. In order to modify and control the color of the fluorescence, it was found necessary to add a third fluorescing agent which is also relatively inert towards the equilibrium between $CeO_2$ and $V_2O_5$. That third fluorescing agent is $Tb_2O_3$ which causes the color of the fluorescence to become a bright yellow. A very slight effect can be discerned with the inclusion of as little as 0.1% by weight $Tb_2O_3$, but generally about 0.3–0.5% is required to produce a noticeable effect. About 1% $Tb_2O_3$ has been deemed to comprise a practical maximum. The concentration of $Tb_2O_3$ required appears to track with the $CeO_2:V_2O_5$ ratio—the concentration of $Tb_2O_3$ increasing as the $CeO_2:V_2O_5$ ratio increases.

Glass-ceramics containing tetrasilicic fluormica as the predominent crystal phase have been demonstrated to be specially suitable for use as dental prosthetic materials. Accordingly, where the proposed application for the inventive color package is dental prosthetic materials, the base glass-ceramic composition will consist essentially, expressed in terms of weight percent as calculated from the batch, of

| $SiO_2$ | 45–70 | $Al_2O_3$ | 0.05–2 |
|---|---|---|---|
| MgO | 8–20 | $ZrO_2$ | 0.5–7 |
| $MgF_2$ | 8–15 | $Al_2O_3 + ZrO_2$ | 1–9 |

A preferred range of tetrasilicic fluormica base compositions consist essentially, expressed in terms of weight percent on the oxide basis, except for fluorine which is expressed in weight percent on the elemental basis, of

| $SiO_2$ | 45–70 | $Al_2O_3$ | 0–2 |
|---|---|---|---|
| MgO | 13–30 | $ZrO_2$ | 0–7 |
| $K_2O$ | 5–20 | BaO | 1–4 |
| F | 4–9 | SrO | 0–5 |

The most preferred base compositions consist essentially, expressed in terms of weight percent on the oxide basis, except for fluorine which is expressed in weight percent on the elemental basis, of

| $SiO_2$ | 55–65 | $Al_2O_3$ | 0.05–2 |
|---|---|---|---|
| MgO | 14–19 | $ZrO_2$ | 0.5–7 |
| $K_2O$ | 8–18 | BaO | 1–4 |
| F | 4–9 | | |

PRIOR ART

U.S. Pat. No. 4,170,823 (Smyth et al.) discloses the use of $Tb_2O_3$ to modify the color of $CeO_2$ fluorescence in conventional dental porcelains. $V_2O_5$ is nowhere mentioned in the patent so there is not even an implication or a suggestion of the operability of the combination of $CeO_2$, $V_2O_5$, and $Tb_2O_3$ to provide a controlled coloration.

DESCRIPTION OF PREFERRED EMBODIMENTS

Table I presents a group of glasses and glass-ceramics illustrating the instant invention. Each of the examples was prepared from the same base composition, that composition being derived from U.S. Pat. No. 4,652,312, supra, the compositions disclosed in that patent being highly desirable because the glass-ceramics prepared therefrom are ideally suited for dental prosthetic applications. That composition consisted essentially, expressed in terms of parts by weight on the oxide basis, except for fluorine which is reported on an elemental basis, of 56.2 parts $SiO_2$, 16.4 parts MgO, 9.8 parts $K_2O$, 4.6 parts $ZrO_2$, 1.8 parts BaO, 1.5 parts SrO, and 6 parts F. Because the sum of the seven components approaches 100, for all practical purposes the individual values may be considered to reflect weight percent. The colorants reported in Table I are presented in parts by weight in excess of the base composition. Because the individual amounts thereof are so small, for all practical purposes those amounts may likewise be deemed to represent weight percent.

The identities of the batch materials for the oxide components are not critical. They may be oxides or other compounds which, when melted together, will be converted into the desired oxide in the proper proportions. For example, $SrCO_3$ and $BaCO_3$ can comprise the sources of SrO and BaO, respectively. The fluorine component was incorporated as $K_2SiF_6$, but KF, $SrF_2$, $MgF_2$, and $BaF_2$ would be operable as batch ingredients.

The batch materials were compounded, thoroughly mixed together to aid in securing a homogeneous melt, and then charged into platinum crucibles. The crucibles were moved into a furnace operating at about 1500° C., held within the furnace for about 2 hours, the resulting melts thereafter poured into steel molds to yield glass slabs having dimensions of about 8"×4"×0.5", and those glass slabs transferred immediately to an annealer operating at about 600° C. After annealing, the color of the slabs was examined in visible light and while being exposed to ultraviolet radiation at a wavelength of 366 nm.

The above description reflects procedures carried out in the laboratory. It must be recognized that the inventive glasses are capable of being melted and formed utilizing conventional commercial glass melting and forming techniques and equipment. It is only necessary that the proper batch be heated to a desired temperature for a sufficient length of time to assure the obtention of a homogeneous melt, and thereafter the melt is formed into a glass shape of a predetermined configuration.

After a visual inspection, the glass slabs were placed in an electrically heated kiln and crystallized in situ to glass-ceramic slabs via heat treatment according to the following schedule:

(1) heated at 100° C./hour from room temperature to 1040° C.;
(2) held at 1040° C. for four hours; and then
(3) cooled to room temperature at furnace rate.

The procedure of cooling at furnace rate involves cutting off the electric current to the kiln and allowing the kiln to cool to room temperature with the slabs retained therewithin. That rate of cooling has been estimated to range about 3°–5° C./minute.

Table I records the colors of the glass-ceramic slabs in visible light and while being exposed to ultraviolet radiation at a wavelength of 366 nm.

TABLE I

|  | 1 | 2 | 3 | 4 | 5 |
|---|---|---|---|---|---|
| $CeO_2$ | — | 0.5 | 1.0 | 1.0 | 1.0 |
| $V_2O_5$ | 0.1 | 0.1 | — | 0.1 | 0.1 |
| $Tb_2O_3$ | — | — | — | — | 0.3 |
| Colors: | | | | | |
| Glass: | | | | | |
| Visible | Clear *Lt. Blue | Clear *Sl Mint Green | Clear *Sl Yellow | *Lt. Straw Yellow | Light Green |
| UV | *Br. Yellow | *Br. Pink | *Br. White | Yellow | *Br. Yellow |

TABLE I-continued

| Glass-Ceramic: | | | | Orange | |
|---|---|---|---|---|---|
| Visible | Mint Green | Bl | White | White | Bl |
| UV | *Br. *Lt. Yellow | *Lt. Gray | Bright White | Bright Orange | Bright Yellow |

|  | 6 | 7 | 8 | 0 | 10 |
|---|---|---|---|---|---|
| $CeO_2$ | 2.0 | 2.0 | 1.0 | 1.8 | 1.5 |
| $V_2O_5$ | 0.1 | 0.08 | 0.1 | 0.12 | 0.1 |
| $Tb_2O_3$ | — | 0.3 | 0.4 | 0.4 | 0.5 |
| $Er_2O_3$ | — | 0.1 | 0.1 | — | 0.15 |
| $Cr_2O_3$ | — | — | — | — | 0.0 ? |
| Colors: | | | | | |
| Glass: | | | | | |
| Visible | Straw Yellow | Light Amber | Light Amber | Light Yellow | Greenish Yellow |
| UV | Yellow | Yellow Orange | Yellow | Yellow | Yellow |
| Glass-Ceramic: | | | | | |
| Visible | A2 | D2 | A1 | A3 | C1 |
| UV | Dull Tan | Medium Yellow | Light Yellow | Medium Yellow | *Br. Gray Yellow |

*Lt. = Light
*Sl. = Slight
*Br. = Bright

The dental colors reported in the above Table are shade tab references offered by dental manufactures as shade guides. The specific colors, viz. A1, A2, A3, B1, C1, and D2, are designations of colors offered by the Vita shade guide, which colors are well known to dentists and dental laboratories and are commercially available.

As can be observed from Table I, the inclusion of $Tb_2O_3$ with $CeO_2$ and $V_2O_5$ assures the development of a yellow coloration in both the precursor glass and in the glass-ceramic, not only when viewed in visible light, but also when subjected to ultraviolet radiation.

In view of the fact that the principal use which is foreseen for the inventive materials is in the field of dental prosthetics, Examples 7–10, containing tetrasilicic fluormica as the predominant crystal phase, are deemed to constitute the most preferred embodiments of the invention.

I claim:

1. A glass-ceramic article having a predominant crystal phase of tetrasilicic fluormica and which exhibits a yellow coloration in visible light and fluoresces with a yellow coloration while being exposed to ultraviolet radiation, said article containing a color package comprising by weight on the oxide basis of 0.05–0.5% $V_2O_5$, 0.25–5% $CeO_2$, and 0.1–1% $Tb_2O_3$ which provides the yellow coloration.

2. A glass-ceramic article according to claim 1 wherein said color package comprises 0.075–0.2% $V_2O_5$, 0.5–2% $CeO_2$, and 0.3–0.5% $Tb_2O_3$.

3. A glass-ceramic article according to claim 1 consisting essentially, in weight percent as calculated from the batch, of 45–70% $SiO_2$, 8–20% MgO, 8–15% $MgF_2$, 5–20% $K_2O$, 0.05–2% $Al_2O_3$, 0.5–7% $ZrO_2$, and 1–9% total $Al_2O_3+ZrO_2$.

4. A glass-ceramic article according to claim 1 consisting essentially, in weight percent on the oxide basis, except for fluorine which is expressed on an elemental basis, of 45–70% $SiO_2$, 13–30% MgO, 5–20% $K_2O$, 4–9% F, 0–2% $Al_2O_3$, 0–7% $ZrO_2$, 1–4% BaO, and 0–5% SrO.

5. A glass-ceramic article according to claim 4 wherein said color package comprises 0.075–0.2% $V_2O_5$, 0.5–2% $CeO_2$, and 0.3–0.5% $Tb_2O_3$.

6. A glass-ceramic article according to claim 4 consisting essentially of 55–65% $SiO_2$, 14–19% MgO, 8–18% $K_2O$, 0–2% $Al_2O_3$, 0.5–7% $ZrO_2$, 4–9% F, and 1–4% BaO.

7. Dental prosthetic materials consisting essentially of glass-ceramic materials having a predominant crystal phase of tetrasilicic fluormica and which exhibit a yellow coloration in visible light and fluoresce with a yellow coloration while being exposed to ultraviolet radiation, said glass-ceramic materials containing a color package comprising, by weight on the oxide basis, of 0.05–0.5% $V_2O_5$, 5–5% $CeO_2$, and 0.1–1% $Tb_2O_3$ which provides the yellow coloration.

8. Dental prosthetic materials according to claim 7 wherein said color package comprises 0.075–0.2% $V_2O_5$ 0.5–2% $CeO_2$, and 0.3–0.5% $Tb_2O_3$.

9. Dental prosthetic materials according to claim 7 wherein said glass-ceramic materials consist essentially, in weight percent on the oxide basis, of 45–70% $SiO_2$, 8–20% MgO, 8–15% $MgF_2$, 5–20% $K_2O$, 0.05–2% $Al_2O_3$, 0.5–7% $ZrO_2$, and 1–9% total $Al_2O_3+ZrO_2$.

10. Dental prosthetic materials according to claim 7 wherein said glass-ceramic materials consist essentially, in weight percent on the oxide basis, of 45–70% $SiO_2$, 13–30% MgO, 5–20% $K_2O$, 4–9% F, 0–2% $Al_2O_3$, 0–7% $ZrO_2$, 1–4% BaO, and 0–5% SrO.

11. Dental prosthetic materials according to claim 10 wherein said glass-ceramic materials contain a color package comprising 0.075–0.2% $V_2O_5$, 0.5–2% $CeO_2$, and 0.3–0.5% $Tb_2O_3$.

12. Dental prosthetic materials according to claim 10 wherein said glass-ceramic materials consist essentially of 55–65% $SiO_2$, 14–19% MgO, 8–18% $K_2O$, 0–2% $Al_2O_3$ 0.5–7% $ZrO_2$, 4–9% F, and 1–4% BaO.

* * * * *